(12) United States Patent
Okihara et al.

(10) Patent No.: US 10,272,212 B2
(45) Date of Patent: Apr. 30, 2019

(54) SYRINGE

(71) Applicant: Terumo Kabushiki Kaisha, Tokyo (JP)

(72) Inventors: Hitoshi Okihara, Fujinomiya (JP);
Shingo Koyama, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/844,144

(22) Filed: Dec. 15, 2017

(65) Prior Publication Data

US 2018/0104422 A1     Apr. 19, 2018

Related U.S. Application Data

(63) Continuation of application No. 14/497,544, filed on Sep. 26, 2014, now Pat. No. 9,861,767, which is a
(Continued)

(30) Foreign Application Priority Data

Mar. 28, 2012  (JP) ................................. 2012-073040

(51) Int. Cl.
| | |
|---|---|
| *A61M 5/50* | (2006.01) |
| *A61M 5/31* | (2006.01) |
| *A61M 5/34* | (2006.01) |

(52) U.S. Cl.
CPC .......... *A61M 5/5086* (2013.01); *A61M 5/344* (2013.01); *A61M 5/347* (2013.01);
(Continued)

(58) Field of Classification Search
CPC ..... A61M 5/5086; A61M 5/344; A61M 5/345
(Continued)

(56) References Cited

U.S. PATENT DOCUMENTS

| | | |
|---|---|---|
| 5,989,227 A | 11/1999 | Vetter et al. |
| 6,196,998 B1 | 3/2001 | Jansen et al. |

(Continued)

FOREIGN PATENT DOCUMENTS

| | | |
|---|---|---|
| DE | 199 56 243 A1 | 5/2000 |
| DE | 10 2008 013 198 A1 | 9/2009 |

(Continued)

OTHER PUBLICATIONS

Chiba et al. Connector, Aug. 2006, pp. 1-4 . Translation of WO 2006087763.*

*Primary Examiner* — Edelmira Bosques
(74) *Attorney, Agent, or Firm* — Foley & Lardner LLP

(57) ABSTRACT

A syringe includes a syringe outer tube including: a tubular-shaped outer tube main body, a reduced diameter section projecting from a distal end of the outer tube main body, and having a distal end opening that is configured to discharge the liquid from the outer tube main body through the reduced diameter section, and a lock adapter concentrically disposed at an outer circumferential portion of the reduced diameter section and configured to be fixed to a mating member; and a cap mounted on the syringe outer tube and including: a cap main body sealing the reduced diameter section in a liquid-tight manner, the cap main body comprising: a base portion including an opening, and a projection projecting into the opening, and a sealing member disposed in the opening, wherein the projection of the base portion contacts a distal end surface of the sealing member.

20 Claims, 8 Drawing Sheets

Related U.S. Application Data continuation of application No. PCT/JP2013/057192, filed on Mar. 14, 2013.

(52) U.S. Cl.
CPC ............. *A61M 2005/312* (2013.01); *A61M 2005/3104* (2013.01); *A61M 2005/3118* (2013.01)

(58) Field of Classification Search
USPC ........................................................ 604/111
See application file for complete search history.

(56) References Cited

U.S. PATENT DOCUMENTS

| | | |
|---|---|---|
| 2009/0082725 A1 | 3/2009 | Witowski |
| 2011/0015578 A1 | 1/2011 | Lowke |
| 2012/0168464 A1 | 7/2012 | Koyama |

FOREIGN PATENT DOCUMENTS

| | | | |
|---|---|---|---|
| EP | 0 716 860 A2 | 6/1996 | |
| EP | 0 917 882 A1 | 5/1999 | |
| EP | 1 600 190 A1 | 11/2005 | |
| JP | 2009-240684 A | 10/2009 | |
| WO | WO 2006087763 A1 * | 8/2006 | ............ A61M 39/12 |
| WO | WO-2010/140019 A1 | 12/2010 | |
| WO | WO-2011/108574 | 9/2011 | |
| WO | WO-2011125475 A1 * | 10/2011 | .......... A61M 5/3129 |

\* cited by examiner

SYRINGE

CROSS-REFERENCE TO RELATED APPLICATIONS

This application is a continuation application filed under 35 U.S.C. 111(a) claiming the benefit under 35 U.S.C. §§ 120 of U.S. patent application Ser. No. 14/497,544, filed Sep. 26, 2014, which is a is a continuation application filed under 35 U.S.C. 111(a) claiming the benefit under 35 U.S.C. §§ 120 and 365(c) of PCT International Application No. PCT/JP2013/057192, filed on Mar. 14, 2013, which is based upon and claims the benefit of priority of Japanese Application No. 2012-073040, filed on Mar. 28, 2012, the entire contents of which are hereby incorporated by reference in their entireties.

BACKGROUND

Technical Field

The present disclosure relates to a syringe.

Background Art

A prefilled syringe in which a sterilized syringe outer tube is filled with a liquid product in an aseptic manner is known (see, for example, WO 2011/108574 A). The prefilled syringe disclosed in WO 2011/108574 A includes: the syringe outer tube having a spout through which the liquid product is ejected, and a lock adapter rotatably supported at the spout; and a cap mounted on the spout of the syringe outer tube. Also, the cap includes a cap main body that seals the spout in a liquid-tight manner, a mounting section disposed on a proximal end side of the cap main body and mounted on an outer circumferential portion of the spout, and a breaking section that links the cap main body with the mounting section and can release the link by breaking.

In this cap, the cap main body is rotated around an axis of the syringe outer tube with respect to the mounting section, thereby breaking the breaking section to separate the cap main body from the mounting section. Further, the cap main body that has been once separated from the mounting section cannot be mounted again on the spout, in other words, the cap main body is configured incapable of recapping the spout. This makes it possible to avoid using the prefilled syringe once opened erroneously, deeming the prefilled syringe as in the unused state.

However, there is a case in the prefilled syringe disclosed in WO 2011/108574 A, where stress that may exceed a breaking limit of the break section breakage is generated at the breaking section when external force is applied to the cap main body at the time of transport, for example. In this case, there is a problem in that the breaking section is undesirably broken.

SUMMARY OF INVENTION

It is an object of embodiments of the present invention to provide a syringe which is excellent in tamperproofness and capable of preventing a breaking section from undesirable breakage.

The above object is implemented by embodiments of the present invention. According to one embodiment, a syringe includes: a syringe outer tube including a tubular-shaped outer tube main body configured to be filled with liquid, a reduced diameter section provided at a distal end portion of the outer tube main body in a projecting manner, through which the liquid is passed, and having an outside diameter more reduced than the outer tube main body, and a ring-shaped lock adapter concentrically disposed at an outer circumferential portion of the reduced diameter section and configured to fix a mating member connected to the reduced diameter section; and a cap including a cap main body mounted on the syringe outer tube and configured to seal the reduced diameter section in a liquid-tight manner when the cap main body is in a mounted state, a ring-shaped mounting section disposed at a proximal end side of the cap main body and mounted on an outer circumferential portion of the lock adapter, and a breaking section that links the cap main body with the mounting section and is capable of releasing the link by breakage. The cap main body includes a ring portion formed on the proximal end side in a projecting manner, and in the mounted state, the ring portion is positioned between the reduced diameter section and the lock adapter and/or on the outer circumferential side of the lock adapter in a loosely-fitted state.

In one aspect, the cap main body includes a plate-like sealing member configured to seal the reduced diameter section in a liquid-tight manner in the mounted state, and the cap main body cannot be mounted again on the syringe outer tube once separated from the mounting section by breakage of the breaking section.

In one aspect, the ring portion includes an inner ring formed on the proximal end side in a projecting manner, and in the mounted state, the inner ring is positioned between the reduced diameter section and the lock adapter in a loosely-fitted state.

In one aspect, the inner ring is formed up to vicinity of a proximal end portion of the lock adapter in a projecting manner.

In one aspect, a separation distance between the inner ring and the reduced diameter section in a radial direction is larger than a separation distance between the inner ring and the lock adapter in a radial direction.

In one aspect, the ring portion includes an outer ring formed on the proximal end side in a projecting manner and linked with the mounting section via the breaking section, and in the mounted state, the outer ring is positioned on the outer circumferential side of the lock adapter in a loosely-fitted state.

In one aspect, the ring portion includes an inner ring and an outer ring formed on the proximal end side in a projecting manner and concentrically disposed, and in the mounted state, the inner ring is positioned between the reduced diameter section and the lock adapter in a loosely-fitted state and also the outer ring is positioned on the outer circumferential side of the lock adapter in a loosely-fitted state.

In one aspect, the breaking section is configured to be broken by rotating the cap main body and the mounting section in relatively opposing directions around an axis of the reduced diameter section, and the mounting section includes a rotation restricting section configured to restrict the lock adapter from rotating around the axis.

In one aspect, the syringe includes a movement restricting section configured to restrict the mounting section from moving in a proximal end direction when the cap main body is separated from the mounting section by breakage of the breaking section.

In one aspect, the outer tube main body is preliminarily charged with liquid.

According to an embodiment of the present invention, in the mounted state in which the cap main body is mounted on the syringe outer tube, the inner ring is positioned between the reduced diameter section and the lock adapter in the loosely-fitted state and also the outer ring positioned outside the lock adapter in the loosely-fitted state. Further, even when the breaking section is broken to separate the cap main body from the mounting section and an attempt is made to mount the cap main body again on the syringe outer tube, the cap main body cannot be mounted again because of this loosely-fitted state. Consequently, the reduced diameter section of the syringe outer tube is surely prevented from being sealed again with the cap main body, which makes it possible to easily confirm that the syringe has already been unsealed. Thus, the syringe is excellent in tamperproofness, and the unsealed syringe is surely prevented from being used by mistake.

Additionally, for example, when an external force is applied to the cap main body at the time of transporting the syringe or the like, the cap main body is tilted relative to the axis of the syringe outer tube and stress that may exceeds the breaking limit of the breaking section breakage is likely to be generated at the breaking section. However, the inner ring and outer ring of the cap main body contact the reduced diameter section and the lock adapter, thereby achieving to prevent or suppress the above mentioned stress from being generated. This prevents the breaking section from undesirable breakage.

DETAILED DESCRIPTION

A syringe according to certain embodiments of the present invention will be described in detail below based on preferred embodiments illustrated in the accompanying drawings.

First Embodiment

Figure 1:
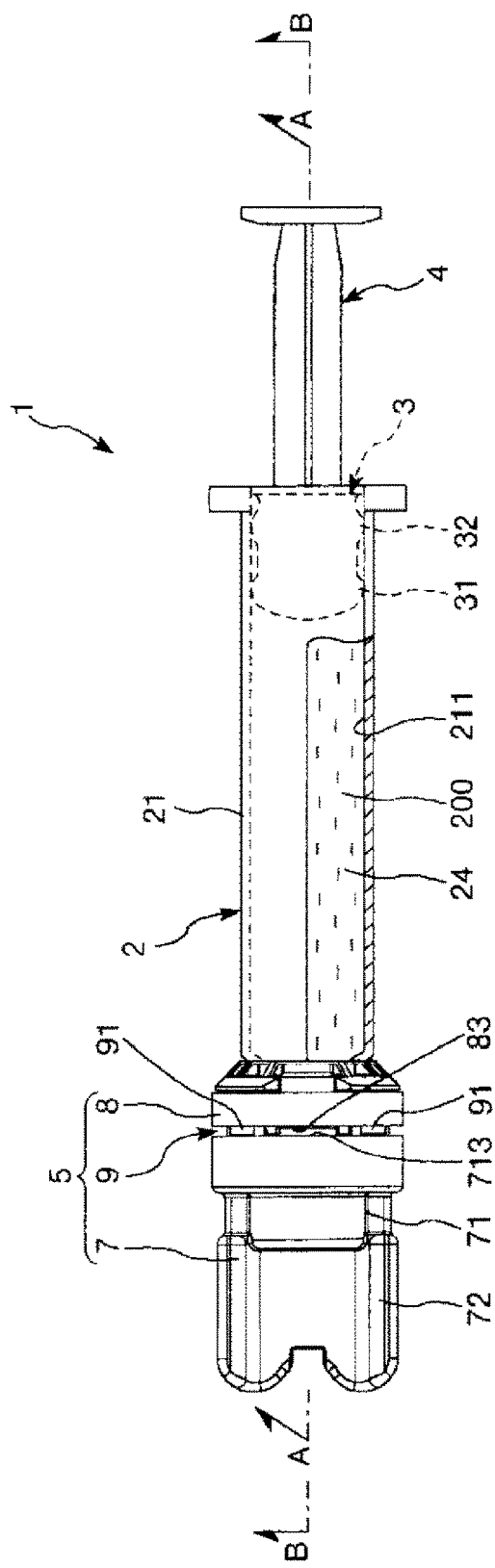
FIG. 1 is a partial longitudinal cross-sectional side view illustrating a syringe according to a first embodiment of the present invention.
Figure 2:
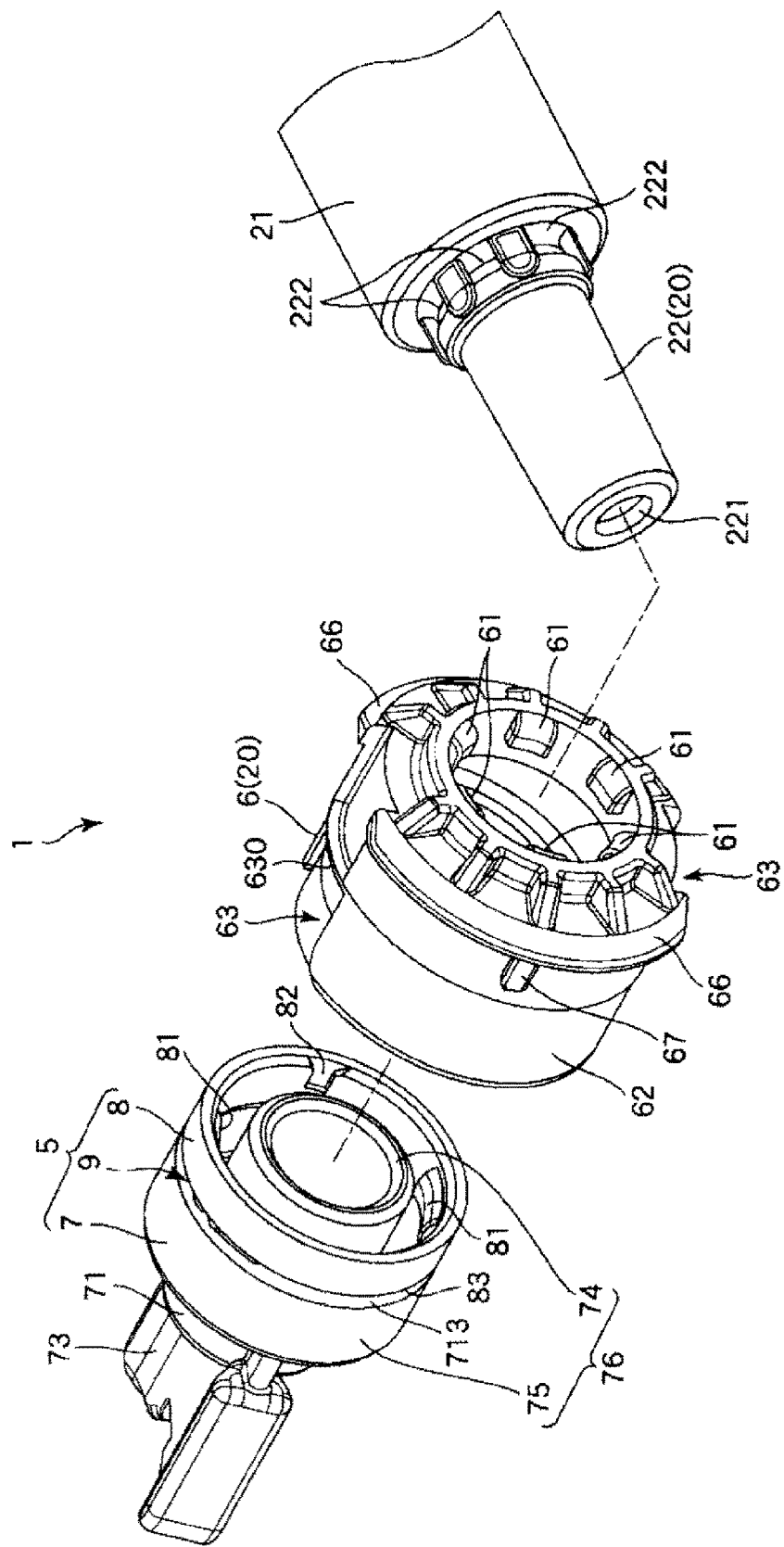
FIG. 2 is an exploded perspective view of a portion on a distal end side of the syringe illustrated in FIG. 1.
Figure 3:
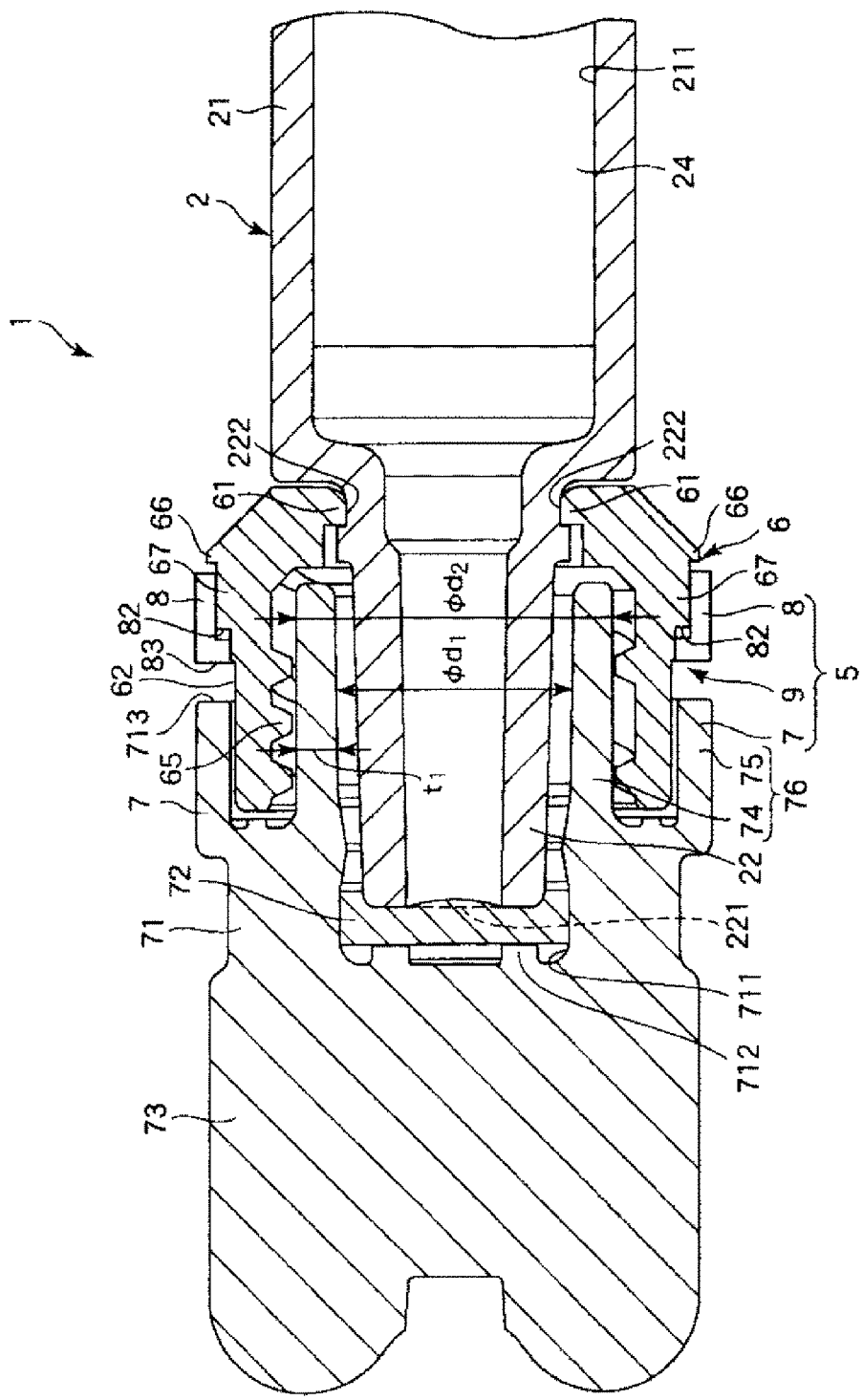
FIG. 3 is a cross-sectional view taken along a line A-A in FIG. 1.
Figure 4:
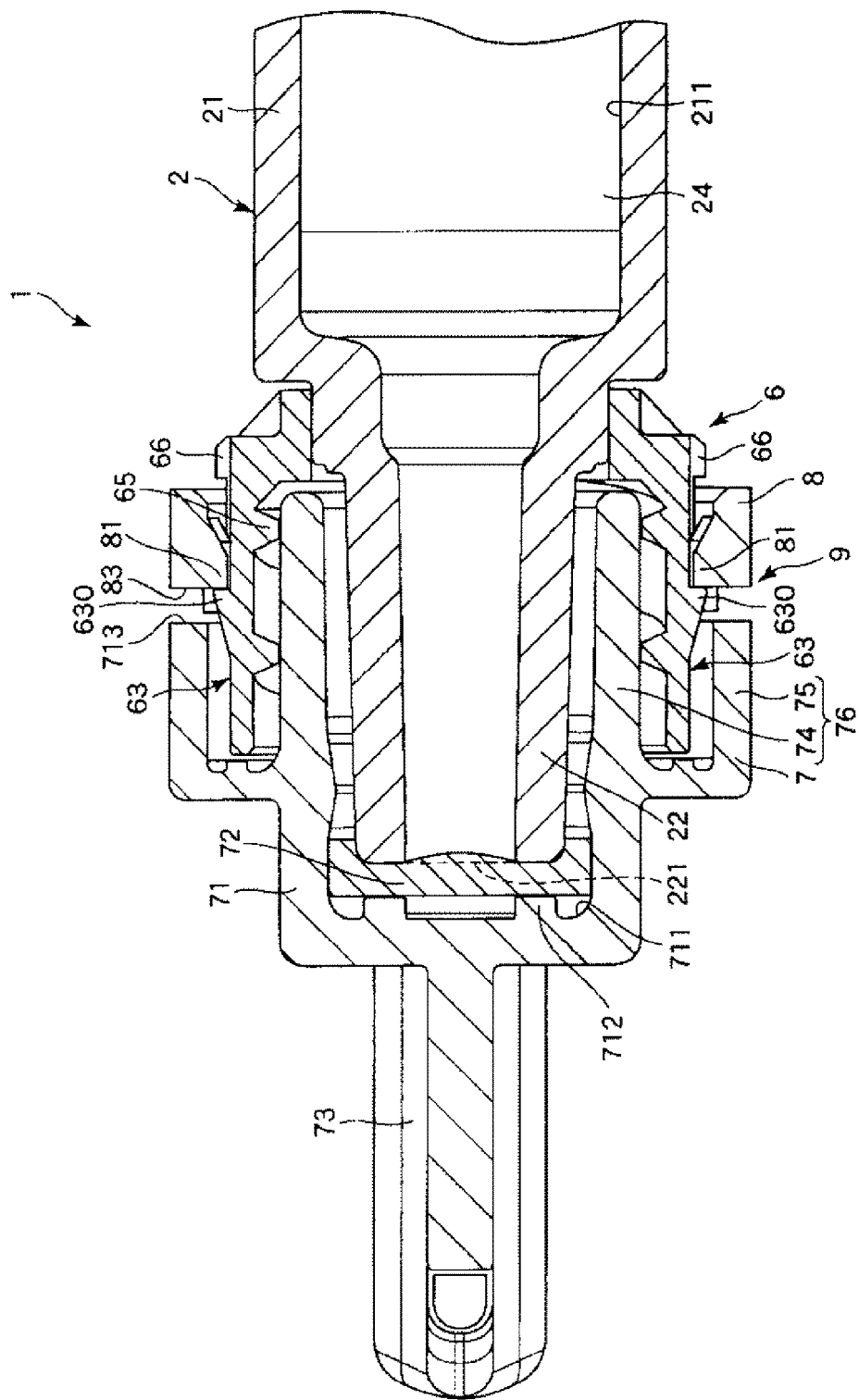
FIG. 4 is a cross-sectional view taken along a line B-B in FIG. 1.
Figure 5:
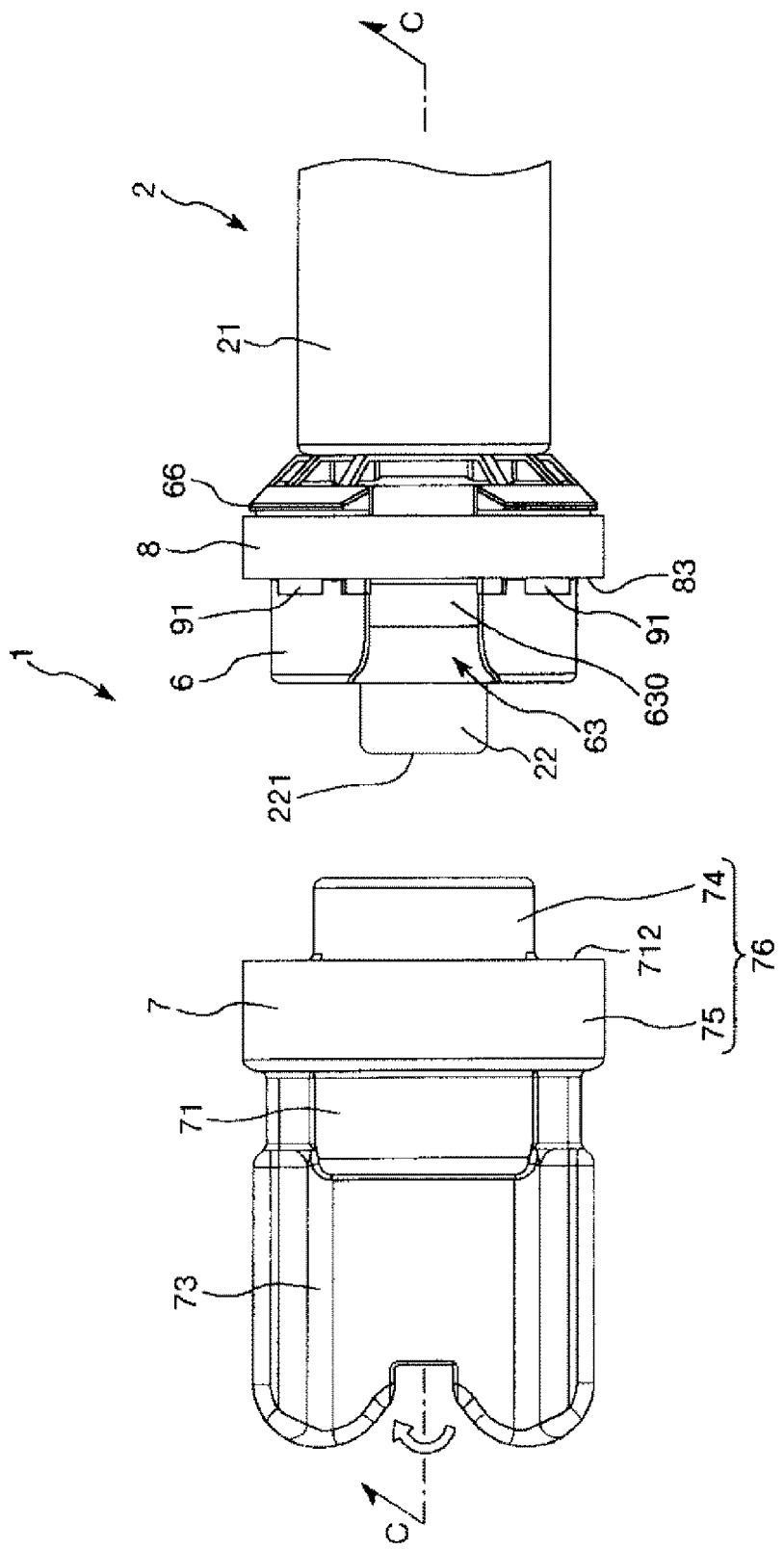
FIG. 5 is a side view illustrating a state in which the syringe illustrated in FIG. 1 is unsealed.
Figure 6:
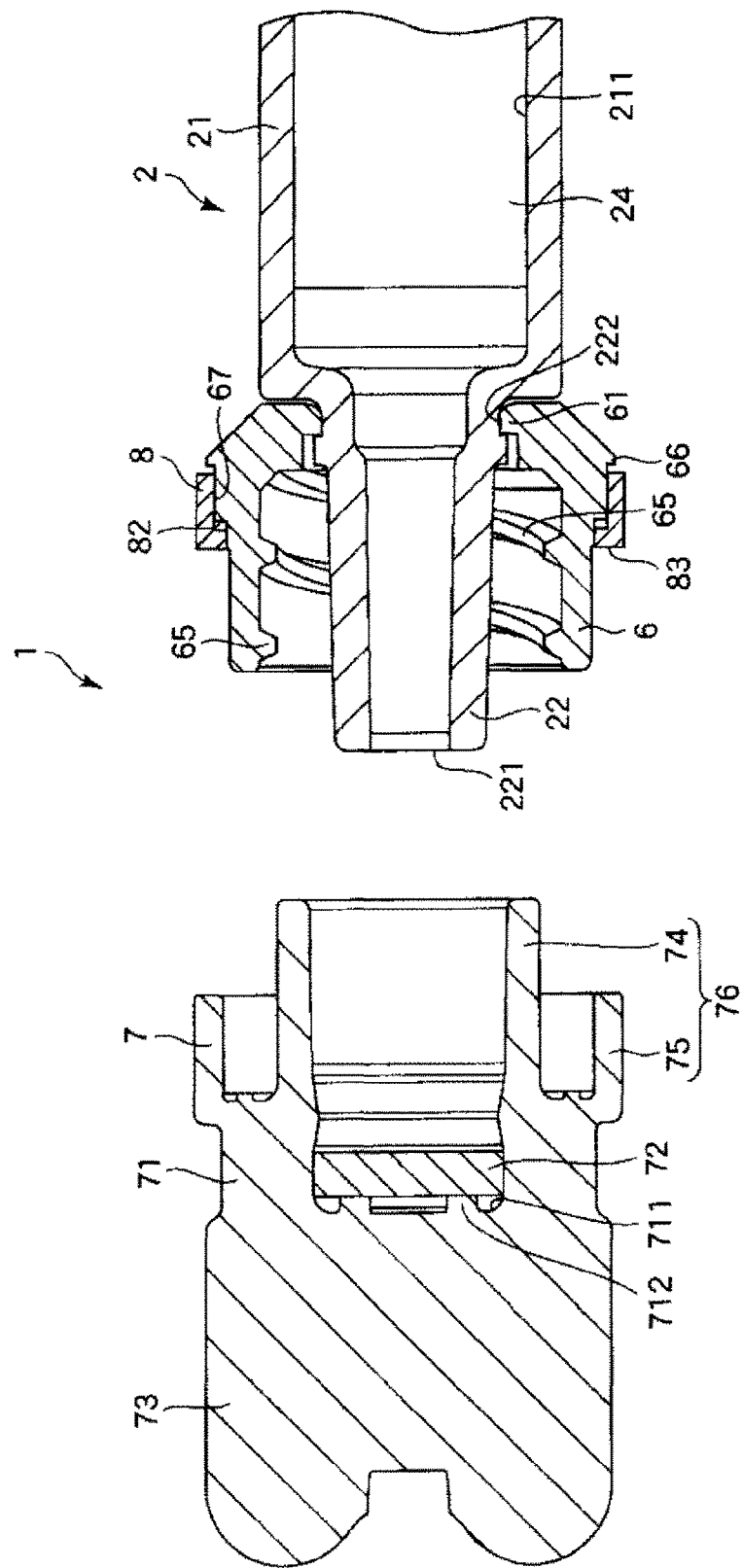
FIG. 6 is a cross-sectional view taken along a line C-C in FIG. 5.

FIG. 1 is a partial longitudinal cross-sectional side view illustrating a syringe according to a first embodiment of the present invention; FIG. 2 is an exploded perspective view of a portion on a distal end side of the syringe illustrated in FIG. 1; FIG. 3 is a cross-sectional view taken along a line A-A in FIG. 1; FIG. 4 is a cross-sectional view taken along a line B-B in FIG. 1; FIG. 5 is a side view illustrating a state in which the syringe illustrated in FIG. 1 is unsealed; FIG. 6 is a cross-sectional view taken along a line C-C in FIG. 5. Incidentally, in the following, the right side in FIGS. 1 to 6 (same in FIGS. 7 and 8) will be referred to as a "proximal end," and the left side as a "distal end" for convenience of description. Further, in FIGS. 3, 4 and 6, a filled liquid product is omitted.

A syringe 1 illustrated in FIG. 1 is a prefilled syringe, which includes a syringe outer tube (hereafter referred to simply as "outer tube") 2, a gasket 3 disposed inside the outer tube 2 so as to be slidable along the longitudinal direction of the outer tube 2, a plunger 4 for moving the gasket 3, and a cap 5 mounted on a distal end portion of the outer tube 2. Further, a space 24 surrounded by the outer tube 2 and the gasket 3 is prefilled with liquid such as a liquid product 200. The cap 5 includes a cap main body 7, a mounting section 8 disposed on a proximal end side of the cap main body 7, and a breaking section 9 that has a function to link the cap main body 7 with the mounting section 8.

The outer tube 2 includes an outer tube main body 21 having a tubular shape, a reduced diameter section 22 provided at a distal end portion of the outer tube main body 21 in a projecting manner and having an outside diameter and an inner diameter more reduced than the outer tube main body 21, and a lock adapter 6 disposed at an outer circumferential portion of the reduced diameter section 22.

The reduced diameter section 22 is integrally formed with the outer tube main body 21. The liquid product 200 passes through the reduced diameter section 22 and is discharged via a distal end opening 221 of the reduced diameter section 22. In the outer tube 2, a spout 20 of the outer tube 2 is formed of the reduced diameter section 22 and the lock adapter 6 whereby a mating member connected to the reduced diameter section 22 is locked. Incidentally, the lock adapter 6 will be described later. Additionally, the mating member to be connected to the reduced diameter section 22 is not specifically limited, but examples of the mating member include a connector disposed at an end or an intermediate portion of a tube, a mouth portion of an infusion bag, and a hub of an injection needle.

The gasket 3 has an elastic body having a cylindrical shape, and has projections 31 and 32 each having an outside diameter of an outer circumferential portion thereof enlarged. The projections 31 and 32 are disposed separately along an axial direction. Further, the projections 31 and 32 slide while keeping close contact with an inner circumferential surface 211 of the outer tube main body 21, thereby securely maintaining gas-tightness (liquid-tightness) of the space 24 and achieving to enhance slidability of the gasket 3.

The plunger 4 is formed of a long member and has a distal end portion thereof screw-engaged with the gasket 3. At the time of discharging the liquid product 200, the plunger 4 is pushed in the distal direction, thereby causing the gasket 3 to push out the liquid product 200 from the reduced diameter section 22 and achieving to easily discharge the liquid product.

As illustrated in FIGS. 2 to 4, the lock adapter 6 constituting the spout 20 of the outer tube 2 is ring-shaped, and concentrically disposed at the outer circumferential portion of the reduced diameter section 22. The lock adapter 6 is for locking the mating member connected to the reduced diameter section 22.

In addition, the lock adapter 6 is supported movable with respect to the reduced diameter section 22 in the axial direction thereof, but restricted from rotating around the axis. For example, according to a configuration illustrated in FIGS. 2 and 3, such a restricting configuration may include a plurality of projections 61 formed on a proximal end inner circumferential portion of the lock adapter 6 in a projecting manner, and recessed portions 222 formed at a proximal end of the outer circumferential portion of the reduced diameter section 22, and each of the projections 61 is inserted into each of the recessed portions 222.

At an outer circumferential portion 62 of the lock adapter 6, a pair of grooves 63 is formed along the axial direction at opposed positions interposing an axis (see FIGS. 2 and 4). Each of the grooves 63 is a portion into which each of projections 81 of the mounting section 8 of the cap 5 described later is inserted respectively.

Further, each of the grooves 63 is formed with a crest portion 630 having an inclined distal end side surface and a vertical proximal end side surface in a middle of the groove formed direction (axial direction). When the cap 5 is pushed toward the outer tube 2 from the distal end side at the time of mounting the cap 5 on the spout 20 of the outer tube 2, the projections 81 of the mounting section 8 are first inserted into the distal end side of the grooves 63, and then moved along a distal end side surface of the crest portion 630, riding over the crest portion 630, and finally are inserted into the proximal end side of the grooves 63.

Thus, when the cap 5 is pushed into the outer tube 2, the cap 5 is easily mounted on the lock adapter 6 (see FIG. 2). Then, in this state, the liquid product 200 can be filled from the proximal end side of the outer tube 2.

Incidentally, once the projections 81 are inserted into the proximal end side of the groove 63, the distal-end side surfaces of the projections 81 contact the proximal end side surfaces of the crest portions 630 even though an attempt is made to move the cap 5 in a direction away from the outer tube 2 (distal end direction). Consequently, further movement of the cap 5 toward the distal end side is restricted. In other words, the projections 81 and the crest portions 630 constitute a distal end direction movement restricting section whereby the mounting section 8 is restricted from moving in a direction to the distal end of the lock adapter 6.

Further, two ribs 66 are formed in a projecting manner on the proximal end side of the outer circumferential portion 62 of the lock adapter 6 along a circumferential direction thereof. The ribs 66 contact the proximal end of the mounting section 8 that has been unsealed (after breakage of the breaking section 9 described later) and movement of the mounting section in the proximal end direction is restricted. In other words, according to the present embodiment, the ribs 66 constitute a proximal end direction movement restricting section (movement restricting section) whereby the mounting section 8 that has been unsealed is restricted from moving in a proximal end direction of the lock adapter 6.

By thus providing the distal end direction movement restricting section and the proximal end direction movement restricting section, the mounting section 8 after breakage is prevented from moving in the axial direction with respect to the lock adapter 6, and collision sound between the mounting section 8 and the lock adapter 6 due to movement thereof can be prevented.

Additionally, on the outer circumferential portion 62 of the lock adapter 6, two projections 67 are formed in a projecting manner along the axial direction on the more distal end side than the ribs 66. Furthermore, on an inner circumferential portion of the mounting section 8, grooves 82 into which respective projections 67 are inserted are formed in a recessing manner along the axial direction. The respective projections 67 are inserted into the corresponding grooves 82 while the cap 5 is mounted on the lock adapter 6. Further, as described above, the respective projections 81 of the mounting section 8 are inserted into the corresponding grooves 63 of the lock adapter 6.

With the above-described configuration, the mounting section 8 (cap 5) can be restricted from rotating around the axis of the lock adapter 6. In other words, according to the present embodiment, a rotation restricting section is formed by combining the projections 67 of the lock adapter 6 with the grooves 82 of the mounting section 8 and combining the grooves 63 of the lock adapter 6 with the projections 81 of the mounting section 8.

As illustrated in FIG. 3 (same in FIG. 4), a female screw 65 is formed on an inner circumferential portion of the lock adapter 6. In the case where the mating member has a male screw, the female screw 65 can be screw-engaged with the male screw. By this screw engagement, the outer tube 2 and the mating member are surely connected to each other.

The materials constituting the outer tube 2 and the plunger 4 are not specifically limited, but examples of the materials include various resins such as polyethylene, polypropylene, polystyrene, polycarbonate, and cyclic polyolefin.

In addition, the material constituting the gasket 3 is not particularly limited, but examples of the material include various rubber materials (especially, vulcanized ones) such as natural rubber, isoprene rubber, butadiene rubber, styrene-butadiene rubber, butyl rubber, silicone rubber, fluororubber, and also include various thermoplastic elastomer, which may be used either singly or as a mixture of two or more thereof.

As illustrated in FIGS. 1, 3 and 4, the cap 5 is mounted on the spout 20 of the outer tube 2 when the syringe 1 is in an unused state (hereafter, this state will be referred to as "mounted state"). Incidentally, in the case where the syringe 1 in this mounted state is used, the cap 5 (cap main body 7) can be rotated and unsealed (see FIG. 5).

As described above, the cap 5 includes the cap main body 7, the mounting section 8 disposed on the proximal end side of the cap main body 7, and the breaking section 9 which has the function to link the cap main body 7 with the mounting section 8 (see FIGS. 1 and 2).

The cap main body 7 includes a disk-shaped base portion 71, a sealing member 72 disposed inside the base portion 71, a grip section 73 provided on a distal end side of the base portion 71, and a ring portion 76 provided on the proximal end side of the base portion 71.

At the base portion 71, a recessed portion 711 open to a proximal end surface is formed and the sealing member 72 is pressed (fitted) into the recessed portion 711. The sealing member 72 is configured to seal the distal end opening 221 of the reduced diameter section 22 constituting the spout 20 in a liquid-tight manner. The sealing member 72 is formed of a disk-shaped elastic body.

Further, on a bottom surface (distal end surface) of the recessed portion 711, a ring-shaped projection 712 contacting the sealing member 72 is formed. With this configuration, in the mounted state, the sealing member 72 is compressed between the projection 712 and the distal end surface of the reduced diameter section 22 of the outer tube 2. Therefore, liquid-tightness at the distal end opening 221 of the reduced diameter section 22 is surely maintained. Further, the thus compressed sealing member 72 biases the cap main body 7 in a distal end direction by own elastic force. This biasing force assists the separation at the time of separating the cap main body 7 from the mounting section 8.

The grip section 73 is a portion to be gripped when the cap main body 7 is rotated to unseal the cap 5. As illustrated in FIGS. 2 and 4, the grip section 73 has a plate-like (flat) shape and formed to be easily gripped.

Further, on the proximal end side of the base portion 71, the ring portion 76 is formed in a projecting manner. The ring portion 76 includes an inner ring 74 formed along an opening edge of the recessed portion 711 of the base portion 71, and an outer ring 75 formed so as to surround an outer circumferential portion of the inner ring 74. In other words, the ring portion 76 includes the inner ring 74 and the outer ring 75 concentrically disposed. Incidentally, the outer ring has a proximal end portion thereof connected to the mounting section 8 via the breaking section 9.

As illustrated in FIGS. 3 and 4, in the mounted state, the inner ring 74 is positioned between the reduced diameter section 22 of the outer tube 2 and the lock adapter 6 in a loosely-fitted state, and also the outer ring 75 is positioned outside the lock adapter 6 in the loosely-fitted state. In other words, in the mounted state, the reduced diameter section 22 is inserted into the inside of the inner ring 74 in the loosely-fitted state, and the distal end portion of the lock adapter 6 is inserted between the inner ring 74 and the outer ring 75 in the loosely-fitted state. Here, "loosely-fitted state" indicates a non-contact state, or indicates a line contact state or a point contact state even in the case of contacting.

Because of this loosely-fitted state, when external force is applied to the grip section 73 of the cap 5 and an entire portion of the cap main body 7 is going to be tilted toward the axis of the syringe 1 (moved laterally) at the time of transporting the syringe 1, for example, the inner ring 74 contacts the outer circumferential portion of the reduced diameter section 22 and the inner circumferential portion of the lock adapter 6, and the outer ring 75 contacts the outer circumferential portion of the lock adapter 6. This can prevent the cap main body 7 from unnecessary tilting movement to the axis of the syringe 1. In the case where the cap main body 7 is tilted, stress that may exceed the breaking limit of the breaking section 9 breakage may be generated at the breaking section 9. However, since the unnecessary tilting of the cap main body 7 is prevented, it is possible to prevent or suppress the stress from being generated. This can preferably prevent undesirable breakage of the breaking section 9, namely, prevents the cap main body 7 from undesirably being separated from the mounting section 8.

The inner ring 74 is, preferably, formed up to the vicinity of the proximal end portion of the lock adapter 6. This allows the proximal end portion of the inner ring 74 to contact the outer circumferential portion of the reduced diameter section 22 and the inner circumferential portion of the lock adapter 6 only when the entire portion of the cap main body 7 is slightly tilted relative to the axis of the syringe 1. This can minimize a tolerable range of the unnecessary tilting of the cap main body 7, and therefore, undesirable breakage of the breaking section 9 can be more surely prevented.

The inner ring 74 has an inside diameter $\phi d_1$ and an outside diameter $\phi d_2$ which are gradually increased in the proximal end direction corresponding to the shape of the reduced diameter section 22. This keeps a thickness $t_1$ of the inner ring 74 substantially constant along the axial direction of the reduced diameter section 22. Thus, since the thickness $t_1$ ($=(\phi d_2-\phi d_1)/2$) of the inner ring 74 is kept substantially constant, strength of the inner ring 74 can be enhanced and the effect of minimizing the tolerable range of tilting the cap main body 7 to the axis of the syringe 1 can be more surely exerted.

Further, a separation distance in a radial direction between the inner ring 74 and the reduced diameter section 22 is, preferably, set larger than a separation distance in a radial direction between the inner ring 74 and the lock adapter 6. This allows the inner ring 74 to contact the inner circumferential portion of the lock adapter 6 before contacting the outer circumferential portion of the reduced diameter section 22 when the entire portion of the cap main body 7 is going to be tilted relative to the axis of the syringe 1. This prevents the inner ring 74 from contacting the outer circumferential portion of the reduced diameter section 22, thereby preventing the outer circumferential portion of the reduced diameter section 22 from being damaged.

In the cap main body 7 having the above-described configuration, the sealing member 72 contacts the distal end opening 221 of the reduced diameter section 22 in the mounted state. As a result, further movement in the proximal end direction is restricted.

Because the sealing member 72 is formed in the disk-like shape, the sealing member 72 contacts the distal end portion of the reduced diameter section 22 in the mounted state. This prevents the sealing member 72 from singly being mounted on the spout 20. Incidentally, the shape of the sealing member 72 is not limited to the disk-like shape and may be a polygonal plate-like shape. Further, on the proximal end surface of the plate-like sealing member 72, a projected portion to be inserted into the distal end opening 221 of the reduced diameter section 22, and a recessed portion to receive the distal end portion of the reduced diameter section 22 may be formed. Incidentally, the above projected portion and recessed portion are formed such that the sealing member 72 is not singly mounted on the spout 20.

On the proximal end side of the cap main body 7, the ring-shaped mounting section 8 is disposed. The mounting section 8 is a member to be mounted on the outer circumferential portion 62 of the lock adapter 6.

As illustrated in FIGS. 2 and 4, the projections 81 are formed on the inner circumferential portion of the mounting section 8 in a projecting manner. Further, preferably, a plurality of the projections 81 is provided; according to the present embodiment, a pair of, namely, two projections 81 are provided. These projections 81 are located opposite to each other interposing the axis of the mounting section 8. In the mounted state, one of the pair of projections 81 is inserted into one of the proximal end side of the grooves 63 of the lock adapter 6, and the other projection 81 is inserted into the other of the proximal end side of grooves 63 of the lock adapter 6.

As illustrated in FIG. 1, the breaking section 9 is provided between the cap main body 7 and the mounting section 8. In the mounted state, the breaking section 9 links a proximal end 713 of the base portion 71 of the cap main body 7 with a distal end 83 of the mounting section 8. Further, as illustrated in FIGS. 5 and 6, when unsealing is executed, more specifically, when the cap main body 7 and the mounting section 8 are relatively rotated around the axis of the syringe 1 (reduced diameter section 22) in opposite directions, the breaking section 9 is broken because applied stress exceeds breaking limit. With this breakage, the link between the cap main body 7 and the mounting section 8 is released.

The breaking section 9 is formed of a plurality of thin portions 91 disposed intermittently around the axis of the cap 5 (mounting section 8). This makes the breaking section 9 to be easily breakable at the time of unsealing.

Incidentally, the number of the thin portions 91 depends on the size and material of the cap 5, but, preferably from two to eight thin portions 91, for example, and more preferably, four to six.

In addition, the thickness of each of the thin portions 91 also depends on the size and the material of the cap 5, but preferably, a thickness of 0.1 to 2.0 mm, for example, and more preferably 0.2 to 0.6 mm.

Incidentally, the material constituting the cap 5 (exclusive of the sealing member 72) is not particularly limited, but for example, the material same as the material constituting the outer tube 2 and the plunger 4 may be used. In this case, at the time of manufacturing the cap 5, it is possible to integrally form the cap main body 7 (exclusive of the sealing member 72), the mounting section 8, and the breaking section 9.

In addition, the material constituting the sealing member 72 is not specifically limited, but, for example, the material same as the material constituting the gasket 3 may be used.

Now, the process from the mounted state to the unsealed state of the cap 5 by rotating the same will be described with reference to FIGS. 3 to 6.

As illustrated in FIGS. 3 and 4, when the syringe 1 is in the unused state, the cap 5 is mounted on the outer tube 2 (spout 20), and the reduced diameter section 22 of the outer tube 2 is sealed by the sealing member 72 in a liquid-tight manner.

Further, in this state, each of the projections 81 of the mounting section 8 of the cap 5 is respectively positioned at the proximal end side of each of the grooves 63 of the lock adapter 6 (see FIG. 4), and each of the projections 67 of the lock adapter 6 is inserted into each of the grooves 82 of the mounting section 8 (see FIG. 3). This prevents the cap 5 from rotating around the axis with respect to the lock adapter 6. Further, each of the projections 61 of the lock adapter 6 is inserted into each of the recessed portions 222 of the outer tube 2. This prevents the lock adapter 6 from rotating around the axis of the outer tube 2. With the above-described configuration, the cap 5 is prevented from rotating around the axis of the outer tube 2.

Further, while the outer tube 2 is gripped by one hand and the grip section 73 of the cap 5 is gripped by the other hand, and the outer tube and the grip section are rotated around the axis of the outer tube 2 in directions opposite to each other. By this rotation, the respective thin portions 91 are twisted. Then, the respective thin portions 91 finally break when the applied stress exceeds the breaking limit (see FIGS. 5 and 6). As a result, the cap main body 7 can be separated, namely, disengaged from the mounting section 8, thereby unsealing the syringe 1.

In addition, when the cap main body 7 is separated, the female screw 65 of the lock adapter 6 of the outer tube 2 is exposed (see FIG. 6). Therefore, the lock adapter 6 can be screw-engaged with the mating member.

Thus, since the cap main body 7 and the mounting section 8 are linked via the respective thin portions 91 in the syringe 1, it is not possible to link the cap main body 7 with the mounting section 8 again when the respective thin portions 91 are broken. Further, as described above, in the mounted state, the inner ring 74 is positioned between the reduced diameter section 22 of the outer tube 2 and the lock adapter 6 in a loosely-fitted state, and also the outer ring 75 is positioned outside the lock adapter 6 in the loosely-fitted state. Additionally, as described above, in the mounted state, the sealing member 72 contacts the distal end portion of the reduced diameter section 22 and configured not to be fitted to the spout 20. In other words, the cap main body 7 is configured not to be fitted to the spout 20. Based on above, mounting (recapping) the cap main body 7 again is surely prevented even when an attempt is made to mount the cap main body 7 on the spout 20 after breakage.

Therefore, it is possible to easily confirm that the syringe 1 has already been unsealed. Accordingly, the syringe 1 is excellent in tamperproofness (property in which a fact that the syringe 1 has once been put into the usable state can be confirmed later), and erroneous use of the syringe 1 which has been once unsealed is surely avoided. Moreover, since the recapping is prevented, even when the unsealed syringe 1 is tampered with, use of the tampered syringe 1 by mistake can be surely prevented.

Second Embodiment

Figure 7:
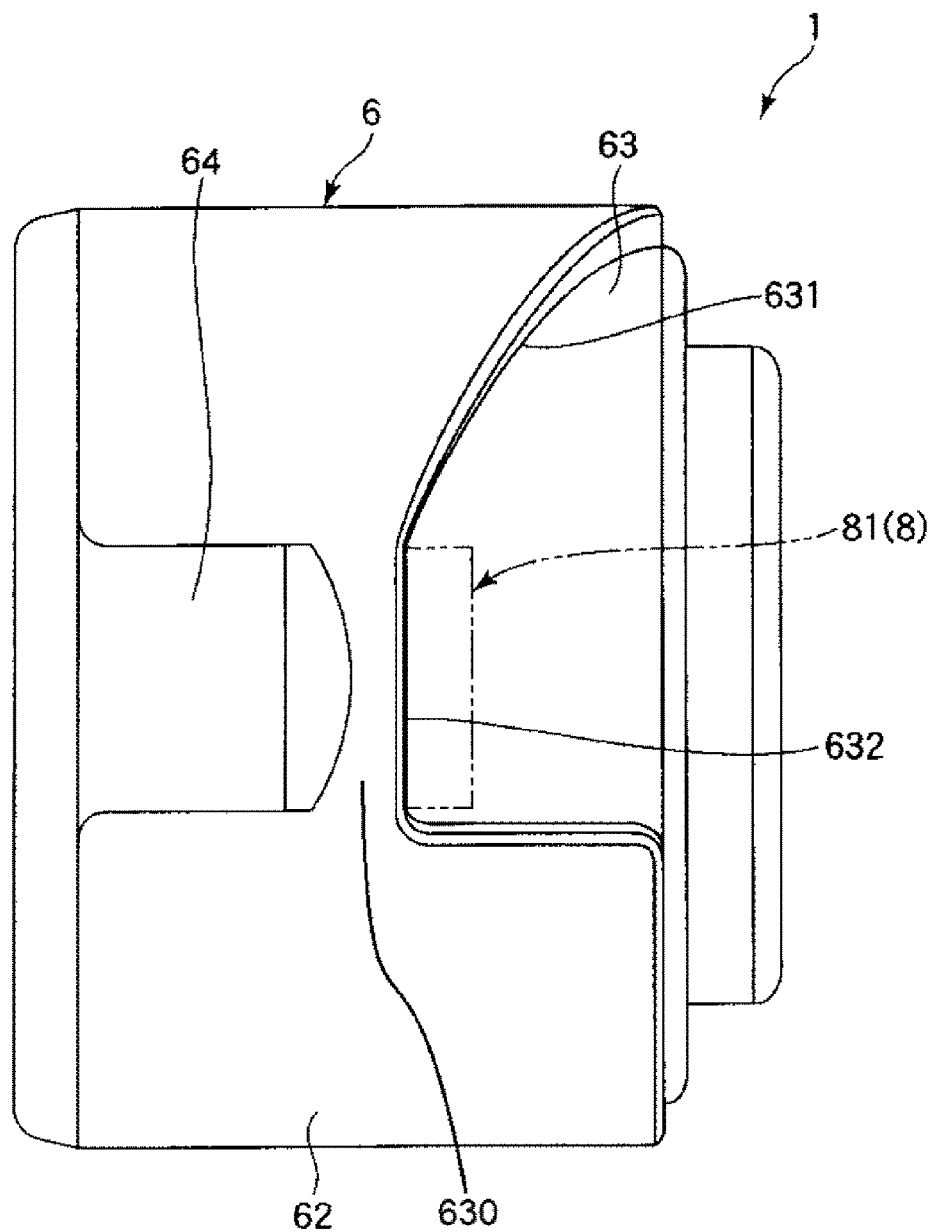
FIG. 7 is a view illustrating a positional relationship between a lock adapter of a syringe outer tube and a mounting section of a cap in a process of unsealing operation at the syringe according to an embodiment of the present invention (second embodiment).
Figure 8:
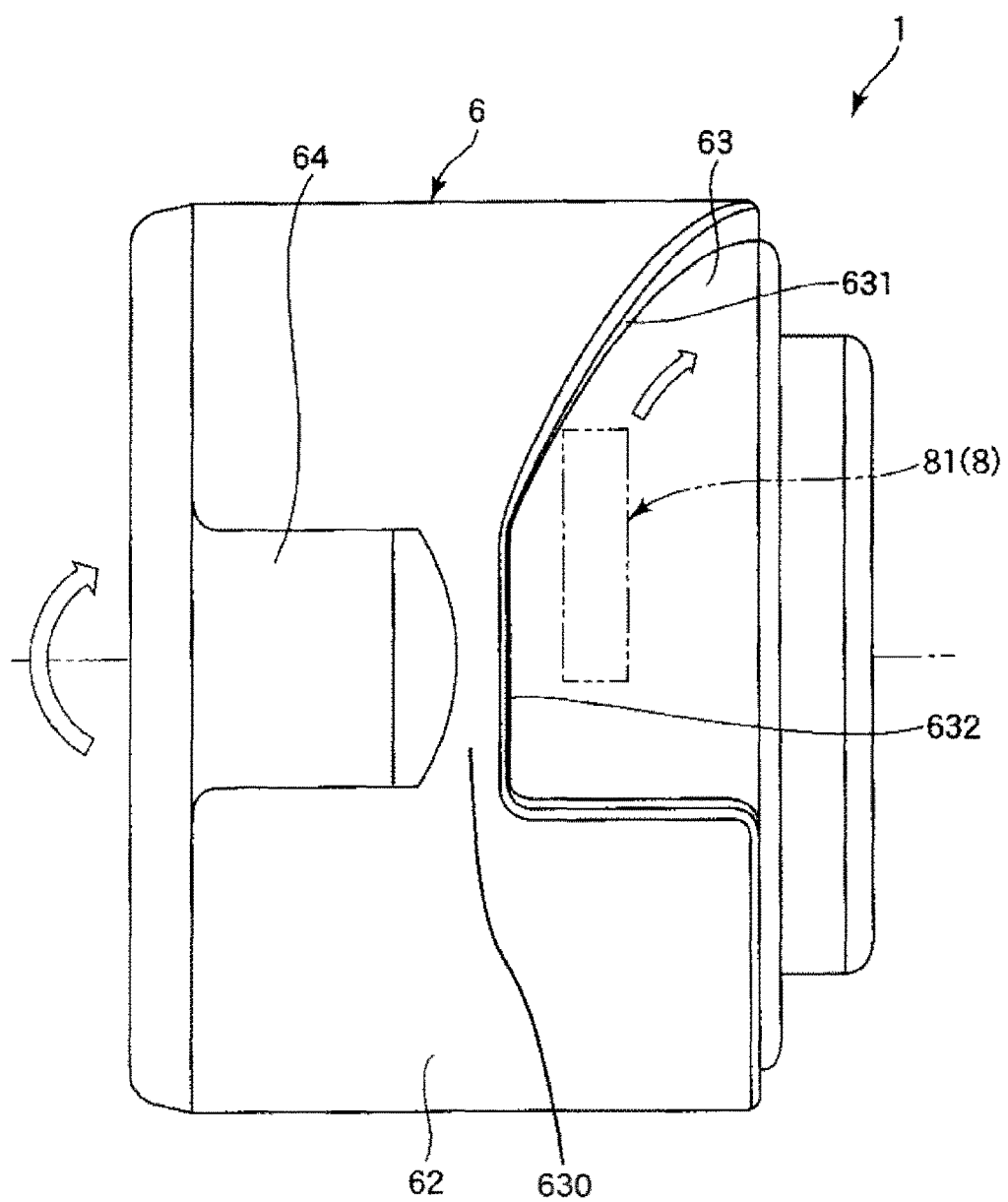
FIG. 8 is a view illustrating a positional relationship between the lock adapter of the syringe outer tube and the mounting section of the cap in the process of unsealing operation at the syringe according to an embodiment of the present invention (second embodiment).

FIGS. 7 and 8 are views illustrating positional relationships between a lock adapter of a syringe outer tube and a mounting section of a cap in a process of unsealing operation at a syringe according to an embodiment of the present invention (second embodiment).

Now, the second embodiment of the syringe according to the present invention will be described below with reference to the drawings. However, description will be given focusing on differences from the above-described embodiment, and description for the same matters same will be omitted.

The present embodiment is the same as the first embodiment except for having a different configuration in the lock adapter.

As illustrated in FIGS. 7 and 8, according to the present embodiment, each of grooves 63 is formed on a more proximal end side than a crest portion 630 of an outer circumferential portion 62 of the lock adapter 6. In a mounted state, each of projections 81 of a mounting section 8 of a cap 5 is inserted into each of the grooves 63.

Incidentally, each of the grooves 63 may be respectively formed on an entire portion of the outer circumferential portion 62 of the lock adapter 6; however, according to this exemplary configuration, the grooves are formed on only a part of the outer circumferential portion 62 in a circumferential direction. In the following, one groove 63 will be representatively described because each of the grooves 63 has the same configuration.

As illustrated in FIG. 7 (also in FIG. 8), the groove 63 can be divided into an inclined section 631 and a perpendicular section 632 continuously formed at the distal end of the inclined section 631. The inclined section 631 is a portion where a side wall of the groove 63 is inclined to an axis of the lock adapter 6. On the other hand, the perpendicular section 632 is a portion where the side wall of the groove 63 is formed in a direction perpendicular to the axis of the lock adapter 6, namely, along a circumferential direction of the outer circumferential portion 62 of the lock adapter 6.

Further, a groove 64 is formed on the outer circumferential portion 62 of the lock adapter 6 at a distal end side of the perpendicular section 632 along the axial direction of the lock adapter 6. When the cap 5 is pushed into an outer tube 2 from a distal end side at the time of mounting the cap 5 on a spout 20 of the outer tube 2, the projection 81 of the mounting section 8 is first inserted into the groove 64, and next rides over a portion (crest portion 630) between the groove 64 and the perpendicular section 632 to be inserted into the perpendicular section 632.

As illustrated in FIG. 7, in a state before unsealing the cap 5, each of the projection 81 is individually positioned at the perpendicular section 632 of the corresponding groove 63. From this state, when the cap main body 7 is rotated around the axis of the outer tube 2, rotational force is also transmitted to the mounting section 8 via each of thin portions 91 and causing each of the projections 81 of the mounting section 8 to move from the perpendicular section 632 to the inclined section 631 as illustrated in FIG. 8. In the case where the cap main body is continuously rotated further, each of the projections 81 of the mounting section 8 moves along the inclined section 631. With this movement, the mounting section 8 is gradually displaced in the proximal end direction, and also each of the thin portions 91 is gradually pulled in the same direction. Further, each of the thin portions 91 finally is broken when applied stress exceeds a breaking limit. As a result, the cap main body 7 can be separated, namely, disengaged from the mounting section 8, thereby unsealing a syringe 1.

As described above, in the cap 5, the pair of projections 81 is located opposing each other interposing the axis of the mounting section 8, and the pair of grooves 63 is formed corresponding to the pair of projections 81 located in this manner. With this configuration, rotating operation can be stably performed when the cap 5 is rotated with respect to the outer tube 2.

In addition, as illustrated in FIGS. 7 and 8, each of the projections 81 of the mounting section 8 can be moved from the perpendicular section 632 to the inclined section 631 of the groove 63, but movement in the opposite direction is restricted. This restricts the direction of the rotating operation, thereby ensuring that the rotating operation is in a correct direction, namely, in an unsealing direction.

Further, as described above, each of the grooves 63 of the lock adapter 6 of the outer tube 2 is formed on a part of the outer circumferential portion 62 in the circumferential direction. In this configuration, the mounting section 8 can be quickly pushed in the proximal end direction and separated from the cap main body 7 at the time of the rotating operation, compared to a case where, for example, each of the grooves 63 is formed on an entire circumference of the outer circumferential portion 62. Consequently, it becomes easy to unseal the syringe 1.

While embodiments of the syringe according to the present invention have been described above with reference to the embodiments illustrated in the drawings, the invention is not limited thereto, and each of the components of the syringe can be replaced by an arbitrary configuration that can exhibit the equivalent function. Further, arbitrary constituent elements may be added.

In addition, embodiments of the syringe according to the present invention may be obtained by arbitrarily combining two or more constituent elements (characteristic features) of the above-described embodiments.

Further, the ring portion includes the inner ring and the outer ring according to the above-described embodiments, but the configuration of the ring portion is not limited thereto and may include only one of the inner ring and the outer ring. In the case where the outer ring is omitted, the inner ring contacts the outer circumferential portion of the reduced diameter section of the syringe outer tube, and the inner circumferential portion of the lock adapter, thereby preventing the cap main body from unnecessary inclination. As a result, undesirable breakage of the breaking section can be avoided. Further, in the case where the inner ring is omitted, the outer ring contacts the outer circumferential portion of the lock adapter, thereby preventing the cap main body from unnecessary inclination. As a result, undesirable breakage of the breaking section can be avoided.

Additionally, the number of ribs constituting the proximal end direction movement restricting section is two according to the first embodiment, but the number thereof is not limited thereto, and may be one, or three or more.

What is claimed is:

1. A syringe comprising:
   a syringe outer tube comprising:
      a tubular-shaped outer tube main body configured to be filled with a liquid,
      a reduced diameter section projecting from a distal end of the outer tube main body, and having a distal end opening that is configured to discharge the liquid from the outer tube main body through the reduced diameter section, and
      a lock adapter concentrically disposed at an outer circumferential portion of the reduced diameter section and configured to be fixed to a mating member; and
   a cap mounted on the syringe outer tube and comprising:
      a cap main body sealing the reduced diameter section in a liquid-tight manner, the cap main body comprising:
         a base portion including an opening, and a projection projecting into the opening, and
         a sealing member disposed in the opening,
         wherein the sealing member comprises a distal end surface and a proximal end surface opposite the distal end surface, and
         wherein the projection of the base portion comprises a proximal end surface that contacts the distal end surface of the sealing member;
      wherein the proximal end surface of the sealing member contacts a distal end surface of the reduced diameter section in a liquid-tight manner and includes:
         a contact portion that contacts the distal end surface of the reduced diameter section, and
         a central portion enclosed by the contact portion;
      wherein the sealing member is compressed between the projection of the base portion and the distal end surface of the reduced diameter section in an axial direction of the cap, such that the contact portion of the proximal end surface of the sealing member is depressed in a distal direction and such that the central portion of the proximal end surface of the sealing member is bulged in a proximal direction and so as to extend into the reduced diameter section via the distal end opening of the reduced diameter section; and
      wherein the sealing member does not extend in the proximal direction beyond a distal end portion of the reduced diameter section and is not fitted to a portion of the reduced diameter section that is proximal of the distal end portion of the reduced diameter section.

2. The syringe according to claim 1,
   wherein the sealing member includes an outer peripheral edge portion that projects outward beyond an outer peripheral portion of the distal end surface of the reduced diameter section, and
   wherein a proximal end surface of the outer peripheral edge portion projects proximal of the distal end surface of the reduced diameter section.

3. The syringe according to claim 1,
   wherein the cap main body further comprises an inner ring disposed between the reduced diameter section and the lock adapter in a loosely-fitted state, and
   wherein the sealing member does not extend between the reduced diameter section and the lock adapter.

4. The syringe according to claim 1,
wherein the cap main body further comprises an inner ring disposed between the reduced diameter section and the lock adapter, and
wherein the inner ring comprises an inner surface that is separated from both the sealing member and the outer circumferential portion of the reduced diameter section, such that an empty space is formed between the reduced diameter section and the inner ring.

5. The syringe according to claim 3, wherein, the inner ring of the cap main body extends to a location proximate a proximal end of the lock adapter.

6. The syringe according to claim 4, wherein the inner ring of the cap main body extends to a location proximate a proximal end of the lock adapter.

7. The syringe according to claim 1, wherein the cap further comprises a ring-shaped mounting section configured to be mounted on the lock adapter.

8. The syringe according to claim 1, wherein the sealing member is configured to be prevented from singly being mounted on the reduce diameter section.

9. The syringe according to claim 1, wherein the sealing member is compressed between the projection of the base portion and the distal end surface of the reduced diameter section so as to bias the cap main body in the distal end direction by an elastic force of the compressed sealing member.

10. The syringe according to claim 1, wherein the projection of the base portion projects in the proximal direction from a proximally-facing surface of the base portion.

11. The syringe according to claim 1, wherein, when the cap is not mounted on the syringe outer tube, the sealing member has a single proximally-facing surface, a single distally-facing surface, and at least one lateral surface extending from the proximally-facing surface to the distally-facing surface.

12. The syringe according to claim 1, wherein, when the cap is not mounted on the syringe outer tube, the sealing member has a shape of a disk or a polygonal plate.

13. A kit comprising:
a syringe outer tube comprising:
  a tubular-shaped outer tube main body configured to be filled with a liquid,
  a reduced diameter section projecting from a distal end of the outer tube main body, and having a distal end opening that is configured to discharge the liquid from the outer tube main body through the reduced diameter section, and
  a lock adapter concentrically disposed at an outer circumferential portion of the reduced diameter section and configured to be fixed to a mating member; and
a cap configured to be mounted on the syringe outer tube and comprising:
  a cap main body structured to seal the reduced diameter section in a liquid-tight manner when the cap is mounted on the syringe outer tube, the cap main body comprising:
    a base portion including an opening, and a projection projecting into the opening, and
    a sealing member disposed in the opening,
    wherein the sealing member comprises a distal end surface and a proximal end surface opposite the distal end surface, and
    wherein the projection of the base portion comprises a proximal end surface that contacts the distal end surface of the sealing member when the cap is mounted on the syringe outer tube;
  wherein the proximal end surface of the sealing member contacts a distal end surface of the reduced diameter section in a liquid-tight manner when the cap is mounted on the syringe outer tube, and includes:
    a contact portion that contacts the distal end surface of the reduced diameter section when the cap is mounted on the syringe outer tube, and
    a central portion enclosed by the contact portion;
  wherein, when the cap is mounted on the syringe outer tube, the sealing member is compressed between the projection of the base portion and the distal end surface of the reduced diameter section in an axial direction of the cap, such that the contact portion of the proximal end surface of the sealing member is depressed in a distal direction and such that the central portion of the proximal end surface of the sealing member is bulged in a proximal direction and so as to extend into the reduced diameter section via the distal end opening of the reduced diameter section; and
  wherein, when the cap is mounted on the syringe outer tube, the sealing member does not extend in the proximal direction beyond a distal end portion of the reduced diameter section and is not fitted to a portion of the reduced diameter section that is proximal of the distal end portion of the reduced diameter section.

14. The kit according to claim 13,
wherein the sealing member includes an outer peripheral edge portion that projects outward beyond an outer peripheral portion of the distal end surface of the reduced diameter section when the cap is mounted on the syringe outer tube, and
wherein a proximal end surface of the outer peripheral edge portion projects proximal of the distal end surface of the reduced diameter section when the cap is mounted on the syringe outer tube.

15. The kit according to claim 13,
wherein the cap main body further comprises an inner ring disposed between the reduced diameter section and the lock adapter in a loosely-fitted state when the cap is mounted on the syringe outer tube, and
wherein the sealing member does not extend between the reduced diameter section and the lock adapter.

16. The kit according to claim 13, wherein the cap main body further comprises an inner ring disposed between the reduced diameter section and the lock adapter, and
wherein the inner ring comprises an inner surface that is separated from both the sealing member and the outer circumferential portion of the reduced diameter section, such that an empty space is formed between the reduced diameter section and the inner ring.

17. The kit according to claim 15, wherein, the inner ring of the cap main body extends to a location proximate a proximal end of the lock adapter when the cap is mounted on the syringe outer tube.

18. The kit according to claim 16, wherein the inner ring of the cap main body extends to a location proximate a proximal end of the lock adapter when the cap is mounted on the syringe outer tube.

19. The kit according to claim 13, wherein the cap further comprises a ring-shaped mounting section configured to be mounted on the lock adapter when the cap is mounted on the syringe outer tube.

20. A method of sealing a distal end opening of a syringe outer tube with a cap, the method comprising:
  providing a syringe comprising:
    a syringe outer tube comprising:
      a tubular-shaped outer tube main body configured to be filled with a liquid,
      a reduced diameter section projecting from a distal end of the outer tube main body, and having a distal end opening that is configured to discharge the liquid from the outer tube main body through the reduced diameter section, and
      a lock adapter concentrically disposed at an outer circumferential portion of the reduced diameter section and configured to be fixed to a mating member; and
  providing a cap comprising:
    a cap main body comprising:
      a base portion including an opening, and a projection projecting into the opening, and
      a sealing member disposed in the opening,
        wherein the sealing member comprises a distal end surface and a proximal end surface opposite the distal end surface,
  mounting the cap on the syringe such that:
    the cap main body seals the reduced diameter section in a liquid-tight manner,
    a proximal end surface of the projection of the base portion contacts the distal end surface of the sealing member;
    the proximal end surface of the sealing member contacts a distal end surface of the reduced diameter section in a liquid-tight manner and includes:
      a contact portion that contacts the distal end surface of the reduced diameter section, and
      a central portion enclosed by the contact portion; and
    the sealing member is compressed between the projection of the base portion and the distal end surface of the reduced diameter section in an axial direction of cap, such that the contact portion of the proximal end surface of the sealing member is depressed in a distal direction and such that the central portion of the proximal end surface of the sealing member is bulged in a proximal direction and so as to extend into the reduced diameter section via the distal end opening of the reduced diameter section, and
    the sealing member does not extend in the proximal direction beyond a distal end portion of the reduced diameter section and is not fitted to a portion of the reduced diameter section that is proximal of the distal end portion of the reduced diameter section.

* * * * *